United States Patent [19]
Bolonick et al.

[11] Patent Number: 5,637,621
[45] Date of Patent: *Jun. 10, 1997

[54] METHODS AND COMPOSITIONS FOR TREATING BOTRYTIS INFECTIONS

[75] Inventors: Joel Bolonick, Albany; Terrance J. Leighton, Lafayette; Ida K. Yu, San Leandro, all of Calif.

[73] Assignee: NZYM, Inc., San Leandro, Calif.

[*] Notice: The term of this patent shall not extend beyond the expiration date of Pat. No. 5,629,348.

[21] Appl. No.: 339,323

[22] Filed: Nov. 14, 1994

[51] Int. Cl.$^6$ .................. C07C 257/12; C07C 277/08; A61K 31/155
[52] U.S. Cl. .................. 514/631; 514/634; 514/636; 514/637; 564/225; 564/230; 564/236; 564/237; 564/238; 564/243; 564/244
[58] Field of Search .................. 564/225, 243, 564/244, 230, 236, 237, 238; 514/631, 634, 636, 637

[56] References Cited

U.S. PATENT DOCUMENTS

| | | | |
|---|---|---|---|
| 2,277,861 | 3/1942 | Ewinsn et al. | 260/564 |
| 2,394,003 | 2/1946 | Newberry et al. | 260/501 |
| 2,891,855 | 6/1959 | Gysin et al. | 71/2.5 |
| 3,235,361 | 2/1966 | Loux | 71/2.5 |
| 3,309,192 | 3/1967 | Luckenbaugh | 71/2.6 |
| 3,927,214 | 12/1975 | Barth | 424/251 |
| 4,546,113 | 10/1985 | Glazer | 514/636 |
| 4,738,980 | 4/1988 | Arcamone et al. | 514/422 |
| 4,912,199 | 3/1990 | Arcamone et al. | 530/331 |

FOREIGN PATENT DOCUMENTS

| | | |
|---|---|---|
| 0 366 066 | 6/1990 | European Pat. Off. . |
| 0 375 414 | 6/1990 | European Pat. Off. . |
| 94 03434 | 2/1994 | European Pat. Off. . |
| 36 06 294 | 2/1986 | Germany . |
| 92 1045 | 6/1992 | WIPO . |
| 92 20698 | 7/1992 | WIPO . |
| 94 08580 | 4/1994 | WIPO . |

OTHER PUBLICATIONS

CA 84:90177z Pyrimidine Carboxylic . . . Symptons. Barth et al., 1976.
CA 104:206932e Antiprotozoal Diamidines. Glazer, 1986.
CA 112:151252r Analogs . . . Pneumonia. Tidwell et al., p. 17, 1990.
CA 114:49434f Biodistribution . . . Salts. Debs et al., p. 413, 1991.
CA 114:101290x Synthesis . . . Carbon–14. Hesk et al., p. 681, 1991.
Browning, 1967, "Agglomeration," *Chemical Engineering*.
Cory et al., 1992, "Structure and DNA Binding Activity of Analogues of 1,5–Bis (4–amidinophenoxy) pentane (Pentamidine)," *J. Med. Chem.* 35:431–438.
Debart et al., 1989, "Synthesis, DNA Binding, and Biological Evaluation of Synthetic Precursors and Novel Analogues of Netropsin," *J. Med. Chem.* 32:1074–1083.

Donkor et al., 1993, "Pentamidine Congners 1. Synthesis of Cis–and Trans–Butamidine Analogues As Anti–*Pneumocystis carinii* pneumonia Agents," *Bioorg & Med Chem Lett. Unknown*:1137–1140.
Finlay et al., 1951, *J. Am. Chem. Soc.* 73:341.
Fryer, J.D. and Evans, S.A., 1968, Weed Control Handbook *unknown*:101–102.
Hudson et al., 1986, "Guanidines with antifungal ( and antibacterial) activity– a review," Int. Pest Control 148–155.
Jones et al., 1990, "Novel Pentamidine Analogs in the Treatment of Experimental *Pneumocystis carnii* Pnemonia," *Antimicrobial Agents Cemotherapy* 34:1026–1030.
Klingman, 1961, *Weed Control as a Science* pp. 81–96.
Mar., 1993, *Advanced Organic Chemistry: Reactions; Mechanisms and Structures* 4th ed.
Marsden, 1950, *Solvents Guide* 2nd ed.
Perry, 1963, *Perry's Chemical Engineer's Handbook* 4th ed. 8–59.
Pilch et al., 1995, "Berenil [1,3–Bis(4'–aimidinophenyl)triazene] Binding to DNA Duplexes and to a RNA Duplex: Evidence for Both Intercalative and Mior Groove Binding Properties," *Biochemistry* 31:9962–9976.
Sisely and Wood, 1964, *Encyclopedia of Surface Active Agents*.
Smith et al., 1990, "Growth Inhibition of *Botyrytis cinera* by compounds interfering with polyamine metabolism.," *Journal of General Microbiology* 136:985–992.
Smith et al., 1990, "Effect of Enzyme Activated Inhibitors on Ornithine Decarboxylase and Growth of *Botrytis cinerea*," *Phytochemistry* 29:1759–1762.

(List continued on next page.)

*Primary Examiner*—Joseph McKane
*Attorney, Agent, or Firm*—Albert P. Halluin; Pennie & Edmonds

[57] ABSTRACT

The invention provides fungicidal compounds having the general formula:

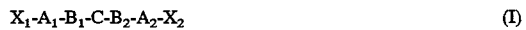

$$X_1\text{-}A_1\text{-}B_1\text{-}C\text{-}B_2\text{-}A_2\text{-}X_2 \qquad (I)$$

wherein $X_1$ is an amidine, a guanidine, or an imidazole group.

$A_1$ is either a five-membered aromatic ring, a six-membered aromatic ring, a fusion of two five-membered aromatic rings, a fusion of 2 six-membered aromatic rings, or a fusion of a six-membered aromatic ring and a five-membered aromatic ring;

$B_1$ is either O (oxygen) or absent; C is a straight chain alkyl comprising 1–8 carbons; $B_2$ is either O (oxygen) or absent; $A_2$ is either a five-membered aromatic ring, a six-membered aromatic ring, a fusion of two five-membered aromatic rings, a fusion of 2 six-membered aromatic rings, or a fusion of a six-membered aromatic ring and a five-membered aromatic ring; and $X_2$ is an amidine, a guanidine, or an imidazole.

7 Claims, 4 Drawing Sheets

OTHER PUBLICATIONS

Tatchell et al., 1989, *Vogel's Textbook of Practical Organic Chemistry 5th Edition.*

Wade et al., Design of Peptides that Bind in the Minor Groove of DNA at 5′–(A,T)G(A,T)C(A,T)–3′ Sequences by a Dimeric Side–by–Side Motif, *J. Am. Chem. Soc.* 114:8783–8794, 1992.

Zimmer et al., 1986, "Nonintercalating DNA– binding ligands: Specificity of the interaction and their use as tools in Biophysical, Biochemical and Biological Investigations of the Genetic Material," *Prog. Biophys. Molec. Biol.* 47:31–112.

METHODS AND COMPOSITIONS FOR TREATING BOTRYTIS INFECTIONS

FIELD OF THE INVENTION

The invention is in the field of agricultural fungicides.

BACKGROUND OF THE INVENTION

Numerous fungal species are capable of acting as pathogens on plants of economic significance. In order to prevent and reduce diseases caused by fungal pathogens, numerous compounds having fungicidal or fungistatic activity have been developed.

The invention described herein pertains to novel classes of compounds for use in inhibiting the growth of pathogenic fungi, particularly Botrytis species, on plants of interest. One plant fungal pathogen of considerable commercial importance is Botrytis. The Botrytis genus comprises several species including: *B. cinera, B. aclada, B. allii, B. squamosa*, etc. *B. cinera* is of particular significance. Botrytis diseases are known to afflict a wide variety of commercially important plants. Plants susceptible to Botrytis infections include: fruits such as strawberries, grapes, apples and blueberries; vegetables, such as beans, cabbage, carrots, cucumbers; and ornamental plants, such as African violet, begonia, chrysanthemum, geranium, rose, and tulip. Botrytis infections may destroy a variety of areas on a plant.

Two embodiments of compounds for use in the subject methods of controlling Botrytis infections, and infections of similar fungal species, are pentamidine and netropsin. Pentamidine has been used to treat several animal parasites; however, the use of pentamidine to treat or prevent fungal infections of plants are unprecedented. Similarly, netropsin has been used to treat bacterial and viral infections in animals; however, the use of netropsin to treat or prevent fungal infections of plants is unprecedented.

SUMMARY OF THE INVENTION

The invention comprises compounds having the general formula:

$$X_1\text{-}A_1\text{-}B_1\text{-}C\text{-}B_2\text{-}A_2\text{-}X_2 \qquad (I)$$

wherein $X_1$ is an amidine, a guanidine, or an imidazole group.

$A_1$ is either a five-membered aromatic ring, a six-membered aromatic ring, a fusion of two five-membered aromatic rings, a fusion of 2 six-membered aromatic rings, or a fusion of a six-membered aromatic ring and a five-membered aromatic ring;

$B_1$ is either O (oxygen) or absent;

C is a straight chain alkyl comprising 1–8 carbons;

$B_2$ is either O (oxygen) or absent;

$A_2$ is either a five-membered aromatic ring, a six-membered aromatic ring, a fusion of two five-membered aromatic rings, a fusion of 2 six-membered aromatic rings, or a fusion of a six-membered aromatic ring and a five-membered aromatic ring; and $X_2$ is an amidine, a guanidine, or an imidazole.

A preferred embodiment of the compounds of formula (I) for use in inhibiting fungal growth is pentamidine.

The invention also provides compounds having the general formula:

where $X_1$ is an amidine group, a guanidine group, or an imidazole;

where Y is 1–5;

where Z is 1–2; and where $X_2$ is an amidine group, a guanidine group, or an imidazole;

A preferred embodiment of compounds of formula (II) is netropsin.

Another aspect of the invention is to provide methods for reducing fungal growth by applying an effective amount of a compound of formula (I) or (II).

The subject methods of reducing fungal growth may be employed either prophylactically or to reduce the growth of fungi already present in the area to be treated. Preferably, the subject methods are used to reduce or prevent the growth of fungal plant pathogens on plants; however, the subject methods may be used to inhibit fungal growth in a variety of non-agricultural applications, e.g. to reduce weathering damage to wood, paint, and the like.

Another aspect of the invention is to provide formulations comprising either a compound of formula (I) or (II) for use in exposing plants to either compounds of formula (I) or (II), respectively. The formulations of the invention comprise an inert carrier and either a compound of formula (I) or (II).

DESCRIPTION OF THE SPECIFIC EMBODIMENTS

The invention described herein provides novel compounds for the reduction of fungal growth, particularly the growth of the plant pathogen, Botrytis. The invention also provides methods of treating fungal infections of plants by applying the compounds of the invention. Another aspect of the invention is to provide novel formulations for application of fungal growth reducing compounds of the invention.

The invention comprises compounds having the general formula:

$$X_1\text{-}A_1\text{-}B_1\text{-}C\text{-}B_2\text{-}A_2\text{-}X_2 \qquad (I)$$

wherein $X_1$ is an amidine, a guanidine, or an imidazole group.

$A_1$ is either a five-membered aromatic ring, a six-membered aromatic ring, a fusion of two five-membered aromatic rings, a fusion of 2 six-membered aromatic rings, or a fusion of a six-membered aromatic ring and a five-membered aromatic ring;

$B_1$ is either O (oxygen) or absent;

C is a straight chain alkyl comprising 1–8 carbons;

$B_2$ is either O (oxygen) or absent;

$A_2$ is either a five-membered aromatic ring, a six-membered aromatic ring, a fusion of two five-membered aromatic rings, a fusion of 2 six-membered aromatic rings, or a fusion of a six-membered aromatic ring and a five-membered aromatic ring; and $X_2$ is an amidine, a guanidine, or an imadazole.

Preferred embodiments of the compound of formula I are capable of specifically binding the minor groove on a double-stranded DNA helix. A particularly preferred embodiment of the compounds of formula (I) for use in inhibiting fungal growth is pentamidine.

The preferred embodiment of the compound of formula (I) is pentamidine. Methods for the synthesis of pentamidine are well known. For example, pentamidine may be synthesized as described in U.K. Pat. No. 567,565, Ashley et al. *J. Chem. Soc.*, 1942, 103, and U.S. Pat. No. 2,394,003 and by numerous variations of these synthesis methods that would be obvious to persons of ordinary skill in the art of organic chemistry. In addition to being able to synthesize pentamidine, the person of ordinary skill in the art may readily synthesize the full range of compounds within the scope of formula (I). The details on such syntheses may be obtained by performing searches of chemical abstracts and through the review of standard texts such as a *Vogel's Textbook of Practical Organic Chemistry* 5th ed, Tatchell et al., John Wiley and Sons, NY, N.Y. (1989), March, *Advanced Organic Chemistry: Reactions, Mechanisms and Structures* 4th ed, John Wiley and Sons, NY, N.Y. (1993), and the like.

The invention also provide compounds having the general formula:

where $X_1$ is an amidine group, a guanidine group, or an imidazole;

where Y is 1–5;

where Z is 1–2; and where $X_2$ is an amidine group, a guanidine group, or an imidazole.

Preferred embodiments of the compound of formula II are capable of specifically binding the minor groove on a double-stranded DNA helix. A particularly preferred embodiment of the compounds of formula (II) is the compound netropsin. Netropsin may be isolated from the bacterium *Streptomyces netropsis*. The preparation of netropsin is described in Finlay et al., *J. Am. Chem. Soc.* 73, 341 (1951). The preparation of netropsin and various minor groove binding derivatives thereof is described in, among other places, Wade et al. *J. A. Chem. Soc.* 114:8783–8794 (1992). A person of ordinary skill in the art of organic chemistry may prepare netropsin as well as other compounds of formula (II) using well known organic synthesis techniques.

Many compounds capable of specifically binding to the minor groove of double-stranded DNA, preferably AT rich regions, may have fungicidal activity, particularly against Botrytis species. In addition to the compounds of formulae I and II, the subject invention specifically contemplates the use of other minor groove DNA binding compounds to treat and/or prevent fungal infections of plants and also contemplates formulations for treating plants that comprise such minor groove DNA binding compounds. Other DNA minor groove binding compounds that can be used in the methods and formulation of the invention include berenil, bis-benzamide, distamycin A, and DAPI (4',6-diamidino-2-phenylindole or 2-[4'-guanyl-phenyl]-6-guanylinole).

The term "minor groove DNA binding" as used herein, refers to the property of preferentially binding to the minor groove of a double-stranded DNA molecule (B form), as opposed to binding to other portions of a double-stranded DNA molecule. A compound having a minor groove DNA binding property may preferentially bind to portions of a DNA molecule comprising particular nucleotide bases, i.e., sequence specific binding, or the minor groove binding may be non-sequence specific. Preferred compounds for use in the treatment and/or prevention of fungal infection have minor groove DNA binding properties similar to that of pentamidine or netropsin.

Dicationic molecules such as pentamidine, Berenil, DAPI, and netropsin bind to DNA targets by selectively interacting with regions of the minor groove. AT-rich regions of the minor groove are preferred binding sites for bis-benzamidines due to the protrusion of the bulky 2-amino group of guanine residues into the minor groove of GC-rich DNA. AT-rich regions of the minor groove have the highest negative electrostatic potential and hence the greatest avidity for dicationic ligands. In addition, van der Waals contacts between aromatic polyamidines and the floor of the minor groove are maximized in AT-rich regions due to the narrowness of AT-rich motifs which increases the strength of van der Waals interactions with aromatic systems. Hydrogen bonding interactions with bases on the floor of the groove are also important to binding affinity. The complimentarity of the curvature of dicationic bis-benzimidazoles with that of the DNA minor groove is also of considerable importance. Molecules with a curvature which closely fits the curvature of the minor groove have the highest target affinity. The above explanation of DNA binding should not be construed as a limitation of the invention. The interaction of aromatic polyamidines (and other molecules) with DNA can be measured by the increase in thermal melting temperature ($\Delta$Tm) following complex formation with synthetic copolymers such as poly dA-dT (Wilson, W. D., Ratmeyer, L., Zhao, M., Strkowski, W. and D. W. Boykin. 1993. *Biochemistry* 32: 4098–4104).

FORMULATION

The compounds of this invention will generally be used in formulation with a liquid or solid diluent or with an organic solvent. The invention specifically provides for numerous formulation comprising either compounds of formula (I) or formula (II) and an inert carrier, such as a diluent. The term "inert" is used to indicate that the carrier does not have significant fungicidal activity. The formulations of the inventions comprise either a compound according to formula (I) or formula (II) and a diluent or surfactant, which may not act as an inert carrier. The formulations may further comprise additional compounds that have fungicidal activity. Useful formulations of the compounds of formula (I) and formula (II) can be prepared in conventional ways. They include dusts, granules, pellets, solutions, emulsions, wettable powders, emulsifiable concentrates and the like. Many of these may be applied directly. Sprayable formulations can be extended in suitable media and used at spray volumes of from about one to several hundred liters per hectare. High strength compositions are primarily used as intermediates for further formulation. The formulations, broadly, contain about 1% to 99% by weight of active ingredient(s) and at least one of a) about 0.1% to 35% surfactant(s) and b) about 5% to 99% solid or liquid inert diluent(s). More specifically, they will contain these ingredients in the following approximate proportions:

| | Active Ingredient | Percent by Weight Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 5–50 | 40–95 | 0–35 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins et al., "Handbook of Insecticide Dust Diluents and Carriers," 2nd Ed., Dorland Books, Caldwell, N.J. The more absorptive diluents are preferred for the wettable powders and the denser ones for dusts. Typical liquid diluents and solvents are described in Marsden, "Solvents Guide," 2nd Ed., Interscience, New York, N.Y., 1950. Solubility under 0.1% is preferred for suspension concentrates; solution concentrates are preferably stable against phase separation at 0° C. "McCutcheon's Detergents and Emulsifiers Annual," MC Publishing Corp., Ridgewood, N.J., as well as Sisely and Wood, "Encyclopedia of Surface Active Agents," Chemical Publ. Co., Inc., New York, N.Y., 1964, list surfactants and recommended uses. All formulations can contain minor amounts of additives to reduce foam, caking, corrosion, microbiological growth, etc. Additives to protect the active compounds against light induced degradation, e.g. photoprotectants, UV screening compounds, and the like are also preferably included in the subject formulations. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon prefoamed granular carriers or by agglomeration techniques. (see, J. E. Browning, "Agglomeration," *Chemical Engineering*, Dec. 4, 1967, pp. 147ff and "Perry's Chemical Engineer's Handbook," 4th Ed., McGraw-Hill, New York, N.Y., 1963, pp. 8–59ff.

For more information regarding the art of formulation, see, for example:

H. M. Loux, U.S. Pat. No. 3,235,361, Feb. 15, 1966, column 6, line 16 through column 7, line 19 and Examples 10 through 41.

R. W. Luckenbaugh, U.S. Pat. No. 3,309,192, Mar. 14, 1967, column 5, line 43 through column 7, line 62 and Examples 8, 12, 15, 39, 41, 52, 53, 58, 132, 138–140, 162–164, 166, 167, 169–182.

H. Gysin and E. Knusli, U.S. Pat. No. 2,891,855, Jun. 23, 1959, column 3, line 66 through column 5, line 17 and Examples 1–4.

G. C. Klingman, "Weed Control as a Science," John Wiley and Sons, Inc., New York, N.Y., 1961, pp.81–96.

J. D. Fryer and S. A. Evans, "Weed Control Handbook," 5th Ed. Blackwell Scientific Publications, Oxford, 1968, pp. 101–103.

METHODS OF USE

The invention provides for novel methods of inhibiting the growth of plant pathogenic fungi, particularly fungi that are species of the genus Botrytis. The methods of the invention comprise the step of applying a compound of either formula (I) or formula (II) to a plant of interest. The compound may be applied to a plant of interest by a variety of means such as spraying a liquid, dusting a powder and the like, well known to the person of ordinary skill in the art of crop protection. The particular method of application selected will be dependent upon a number of factors such as the type of plant, the formulation selected, the arrangement of plants in the field, weather conditions, and the like. The actual amount of fungal growth inhibiting compound applied to each plant may be varied so as to achieve the desired degree of growth inhibition. Optimal dosage for a given plant for a given pathogen, under a given set of environmental conditions may be determined through routine experimentation in which the dosage is systematically varied.

The invention may be better understood by referring to the following examples. The following examples are offered for the purpose of illustrating the invention and should not be interpreted as a limitation of the invention.

EXAMPLES

Example 1

Several compounds were tested for their fungicidal activity against a variety of fungi that are plant pathogens. The compounds were dissolved in a 5% solution of polyethylene glycol and sprayed onto plants and dried at 24° C. The plants were then inoculated with the indicated pathogen one or two days later. After a period of five to eleven days, the presence of disease was assessed. The extent of protection is indicated on a linear scale 0 (no protection) to 10 (100% protection). Pentamidine and netropsin were the most effective of the compounds tested. Concentration is given in parts per million (ppm).

| Compound | Concentration | B. cinerea apple fruit | B. cinerea grape foliar | C. arachidicola peanut foliar | P. oryzae rice foliar | V. inaequalia apple foliar | S. nodorum wheat foliar | P. teres barley foliar |
|---|---|---|---|---|---|---|---|---|
| Pentamidine | 200 | 9 | 9 | 3 | 0 | 7 | 8 | 8 |
|  | 60 | 9 | 8 | 0 | 0 | 3 | 6 | 7 |
|  | 20 | 8 | 7 | 0 | 0 | 0 | 4 | 3 |
|  | 6 | 7 | 6 | 0 | 0 | 0 | 0 | 0 |
|  | 2 | 0 | 1 | 0 | 0 | 0 | 0 | 0 |
| Netropsin | 200 | 10 | 0 | 0 | 0 | 0 | 3 | 0 |
|  | 60 | 9 | 0 | 0 | 0 | 0 | 0 | 0 |
|  | 20 | 8 | 0 | 0 | 0 | 0 | 0 | 0 |
|  | 6 | 6 | 0 | 0 | 0 | 0 | 0 | 0 |
|  | 2 | 0 | 0 | 0 | 0 | 0 | 0 | 0 |

Example 2

Pentamidine on Strawberries

Field tests were conducted to evaluate the ability of pentamidine to control Botrytis infections of strawberries. Plant toxicity was also evaluated. Randomized complete blocks of strawberries, with four replications for each treatment. Pentamidine was tested at low (50 ppm) and high (200 ppm) dose rates in a formulation comprising a tri-methyl ether of polyethylene glycol. A commercial Botrytis fungicide, Ronoral (the active ingredient is iprodione), was applied at the high label rate as a "positive control." Treatment applications were repeated every fourteen days.

Mean berry weight per plot from eight weekly harvests was taken as the disease end point.

Figure 1:
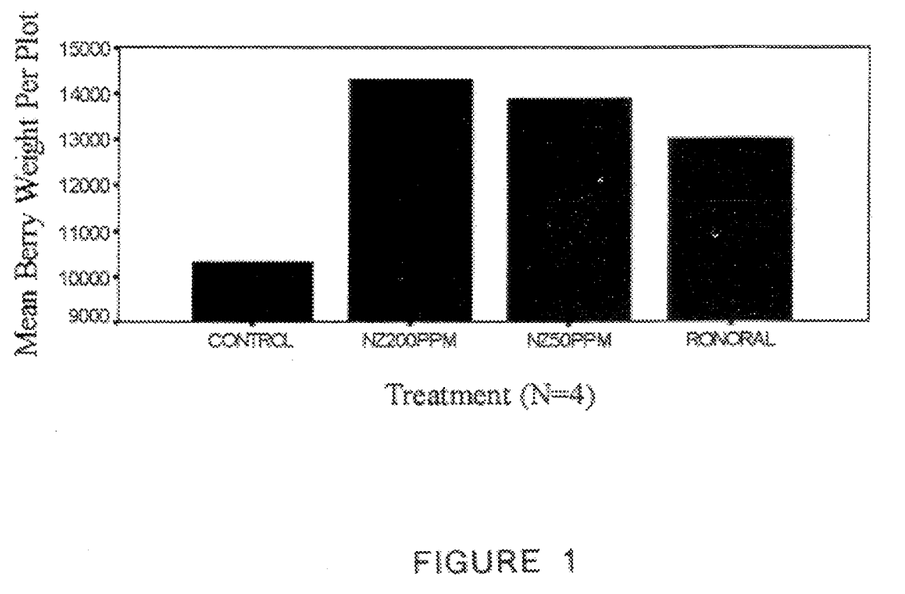
FIG. 1 is a graph showing the protective effects of pentamidine against Botrytis on strawberries.

No pentamidine flower, shoot, or leaf phytotoxicity was observed at either the low or high application rates. Pentamidine applied at 50 ppm produced a 34% increase in strawberry production. Pentamidine applied at 200 ppm produced a 38% increase in strawberry production. Ronoral applied at the high label rate produced a 26% increase in strawberry production. An SPSS statistical model of the data was been created. The mean berry weight per plot data is shown in FIG. 1.

Figure 2:
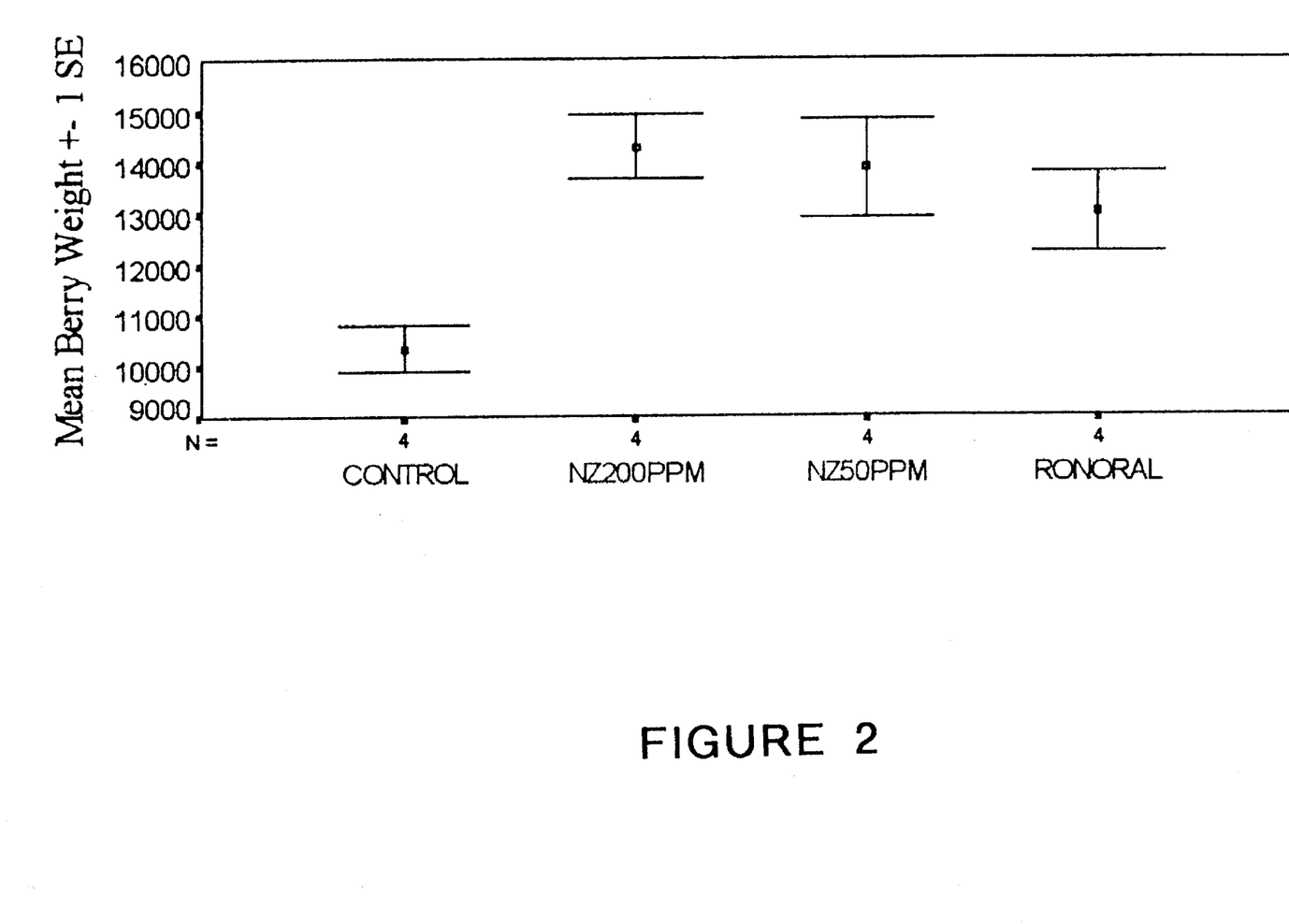
FIG. 2 is a graph showing the effect of pentamidine on Botrytis infected strawberries. NZ200 ppm refers to pentamidine at a concentration of 100 parts per million. NZ50 ppm refers to pentamidine at a concentration of 50 parts per million.

The increased strawberry production data obtained in this study was highly significant statistically. FIG. 2 is a plot of the mean berry weight data±one standard error of the mean. All of the treatments are well outside of the standard error of the untreated control group.

Example 3

Pentamidine on Zinfandel Grapes

Field tests were conducted to evaluate the ability of pentamidine to control Botrytis. Randomized complete blocks of zinfandel vines, with six replications for each treatment. Pentamidine was tested in a dose-ranging series from 2–100 ppm in a formulation comprising a tri-methyl ether of polyethylene glycol. A commercial Botrytis fungicide, Ronoral, was applied at the high label rate as a "positive control." Botrytis protection was assessed in naturally infected fruit clusters, and in fruit clusters which were sprayed with the treatment, and subsequently challenged by spraying with $10^5$ spores per ml of field isolated Botrytis spores.

Figure 3:
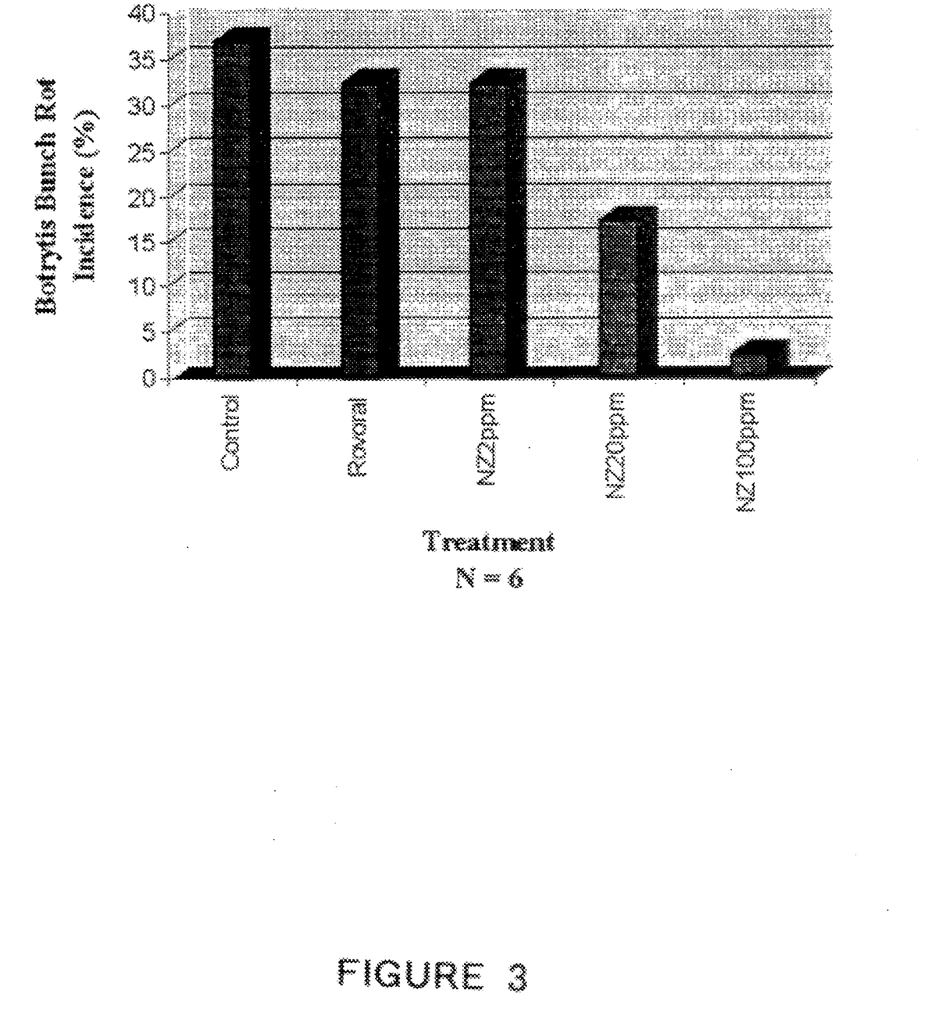
FIG. 3 is a graph showing the effect of pentamidine on Botrytis infected zinfandel grapes. Bunch rot is measured. NZ100 ppm refers to pentamidine at a concentration of 100 parts per million. NZ20 ppm refers to pentamidine at a concentration of 20 parts per million. NZ2 ppm refers to pentamidine at a concentration of 2 parts per million.
Figure 4:
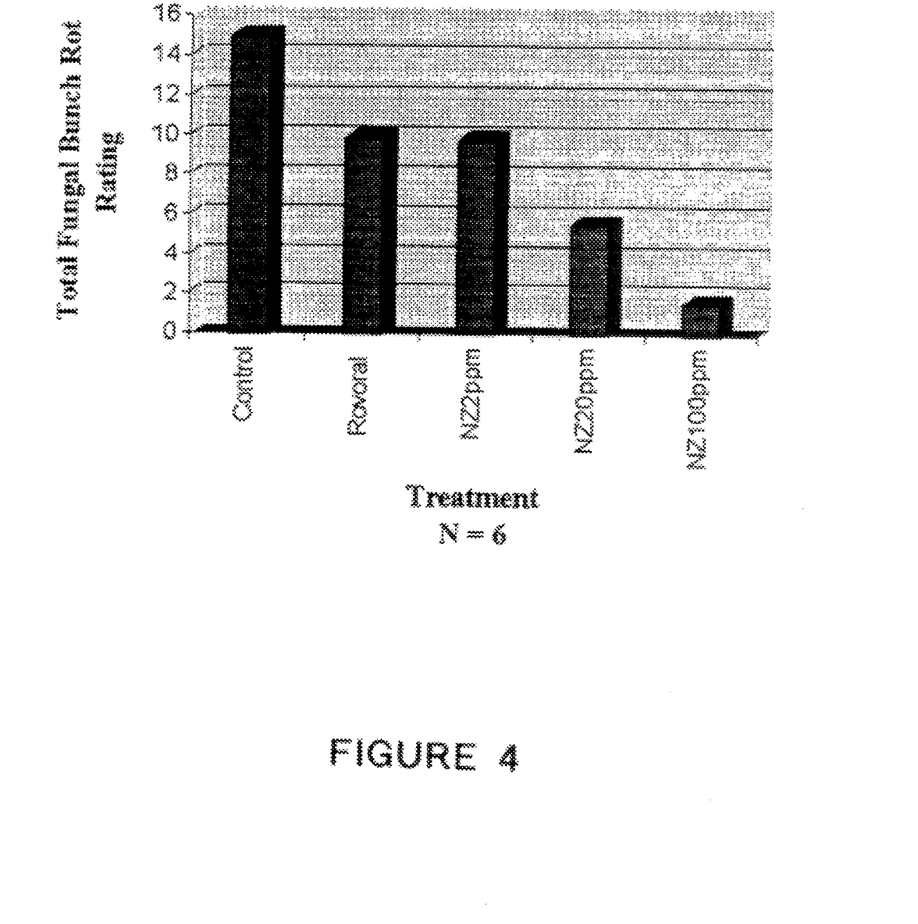
FIG. 4 is a graph showing the effect of pentamidine on Botrytis infected zinfandel grapes. Bunch rot is measured. NZ100 ppm refers to pentamidine at a concentration of 200 parts per million. NZ20 ppm refers to pentamidine at a concentration of 20 parts per million. NZ2 ppm refers to pentamidine at a concentration of 2 parts per million.

Disease end points as given in FIGS. 3 and 4. Incidence equals percent of examined clusters which had fungal rot. Severity equals percent of infected berries within each cluster. Incidence*severity equals total bunch rot rating.

No pentamidine flower, shoot, or leaf phytotoxicity was observed at any application rate. It was recognized at the start of the field trial that 1994 growing conditions did not seem conducive to high rates of "natural" Botrytis infections. A Botrytis spore challenge inoculum was used to replicate previous greenhouse protocols, and to insure that a statistically significant disease incidence would be obtained during the study. As expected, at the end of the study, uninoculated vines had a three- to five-fold lower incidence of Botrytis infection than inoculated vines. The effects of pentamidine treatment on Botrytis bunch rot incidence is shown in FIG. 3. Pentamidine at 2 ppm gave comparable protection to high label rates of Ronoral, and substantially greater protection than Ronoral at 20 ppm. The antifungal effects of pentamidine are well correlated with the application rate.

An emerging problem with Ronoral and other existing Botrytis fungicides, is the "superinfection" of clusters by Aspergillus and Penicillium following fungicide application. Overgrowth of these undesirable fungi is thought to be due to the detrimental effects of existing fungicides on beneficial non-target yeasts and fungi, which normally suppress the growth of Aspergillus and Penicillium. The selectivity of pentamidine for Botrytis, which was observed in the greenhouse, was also demonstrated in this field study. A measurement of the total fungal rot rating (Botrytis, Aspergillus, and Penicillium) demonstrate that pentamidine applied at 2 ppm performs as well as the high label rate of Ronoral, and that pentamidine at 20 ppm substantially outperforms Ronoral. These data are shown in FIG. 4.

INCORPORATION BY REFERENCE

All patents, patents applications, and publications cited are incorporated herein by reference.

Equivalents

The foregoing written specification is considered to be sufficient to enable one skilled in the art to practice the invention. Indeed, various modifications of the above-described modes for carrying out the invention which are obvious to those skilled in the field of organic chemistry or related fields are intended to be within the scope of the following claims.

What is claimed is:

1. A method of treating or preventing a fungal infection, said method comprising the step of applying to a plant an effective amount of a compound having the formula:

(I)

wherein $X_1$ is amidine or guanidine;

$A_1$ is a five-membered aromatic ring, a six-membered aromatic ring, a fusion of two five-membered aromatic rings, a fusion of two six-membered aromatic rings or a fusion of a five-membered aromatic ring and a six-membered aromatic ring;

$B_1$ is oxygen or absent;

C is a straight-chain alkyl comprising 1-8 carbons;

$B_2$ is oxygen or absent;

$A_2$ is a five-membered aromatic ring, a six-membered aromatic ring, a fusion of two five-membered aromatic rings, a fusion of two six-membered aromatic rings or a fusion of a five-membered aromatic ring and a six-membered aromatic ring; and $X_2$ is amidine or guanidine.

2. The method of claim 1, wherein the fungal infection is caused by Botrytis.

3. The method of claim 2, wherein $B_1$ and $B_2$ are each oxygen.

4. The method of claim 2, wherein $X_1$ and $X_2$ are each amidine or guanidine.

5. The method of claim 4, wherein the compound is pentamidine.

6. The method of claim 5, wherein the plant is a strawberry plant.

7. The method of claim 5, wherein the plant is a grape plant.

* * * * *